United States Patent [19]
Beran et al.

[11] Patent Number: 5,404,751
[45] Date of Patent: Apr. 11, 1995

[54] METHOD AND APPARATUS FOR MEASURING THE PEEL STRENGTH OF AN ADHESIVELY BONDED PAPER JOINT

[75] Inventors: Robert L. Beran; Steven P. Metzler, both of Covington, Va.

[73] Assignee: Westvaco Corporation, New York, N.Y.

[21] Appl. No.: 282,550

[22] Filed: Jul. 29, 1994

[51] Int. Cl.6 ............................................. G01N 3/24
[52] U.S. Cl. .................... 73/150 A; 73/826; 73/827; 73/853
[58] Field of Search ............. 73/150 A, 826, 827, 73/853, 857

[56] References Cited

U.S. PATENT DOCUMENTS

| | | |
|---|---|---|
| 2,979,944 | 4/1961 | Abbott . |
| 3,396,578 | 8/1968 | Skundberg . |
| 3,577,775 | 5/1971 | Henderson ........................ 73/827 |
| 3,850,033 | 11/1974 | Schmitt . |
| 4,010,641 | 3/1977 | Krieger, Jr. . |
| 4,080,825 | 3/1978 | Liebrenz et al. . |
| 4,475,404 | 10/1984 | Rutledge, Jr. et al. ............ 73/827 |
| 4,624,144 | 11/1986 | Strimel ........................... 73/826 |
| 4,787,952 | 11/1988 | Broz et al. . |
| 4,856,325 | 8/1989 | Tomita et al. . |
| 4,862,740 | 9/1989 | Lanier . |
| 4,893,513 | 1/1990 | Schroeder et al. . |
| 4,957,004 | 9/1990 | McKinlay et al. . |
| 5,111,701 | 5/1992 | Klein . |
| 5,176,028 | 1/1993 | Humphrey ..................... 73/150 A |
| 5,201,230 | 4/1993 | Sakakibara . |

Primary Examiner—Richard E. Chilcot, Jr.
Assistant Examiner—Max H. Noori
Attorney, Agent, or Firm—J. R. McDaniel; R. L. Schmalz

[57] ABSTRACT

This invention relates to an apparatus and method for measuring the peel strength of a paper joint which is adhesively bonded. Such structures of this type, generally, allow the peel strength of the adhesively bonded joint to be accurately and repeatably measured in an inexpensive manner.

20 Claims, 4 Drawing Sheets

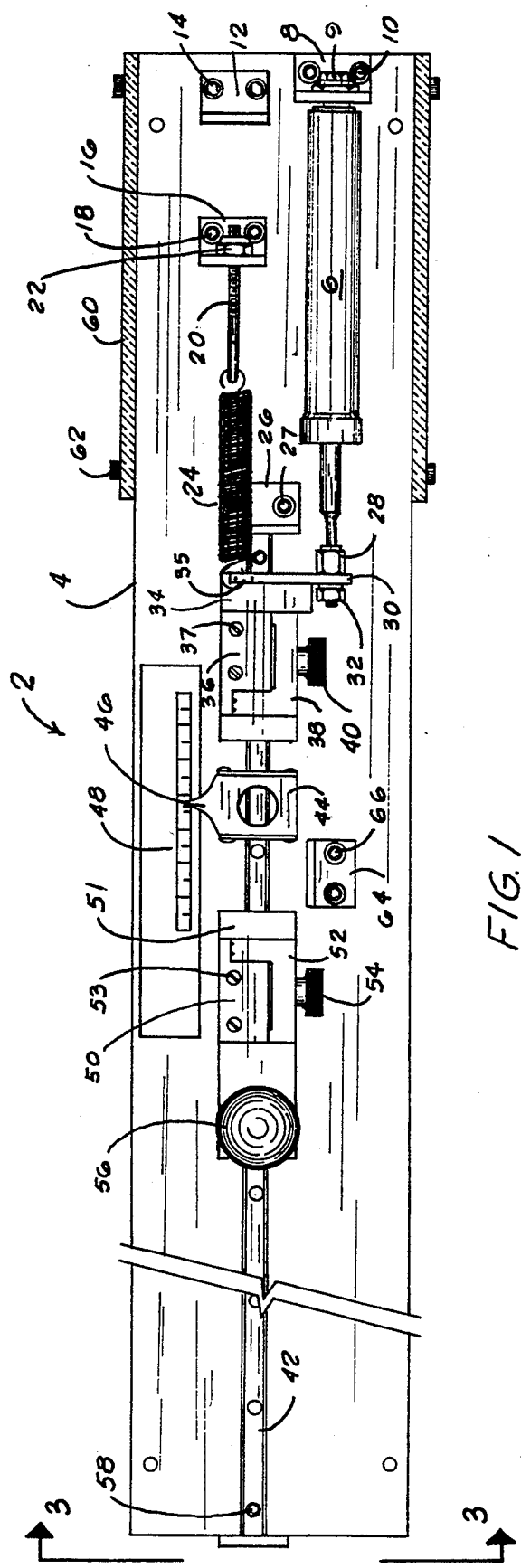
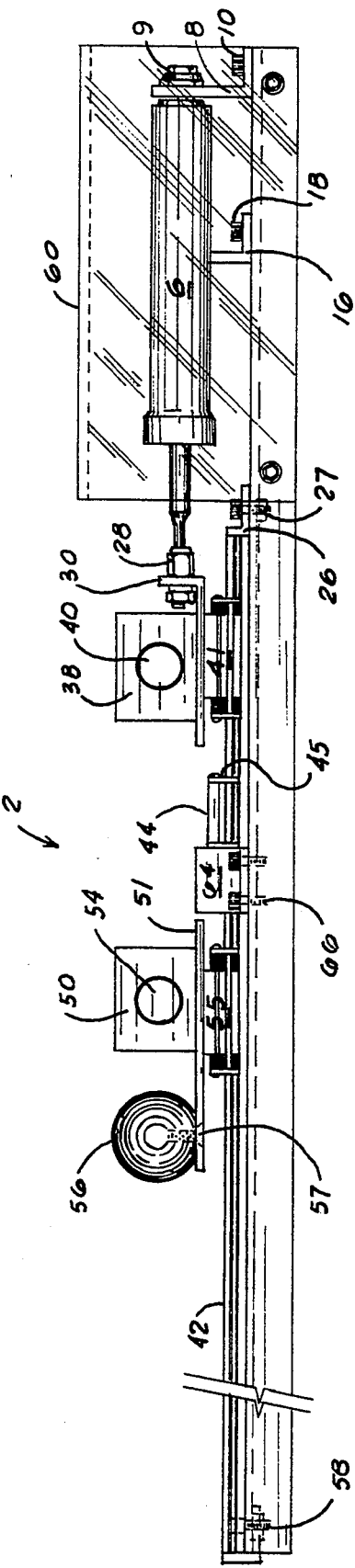
FIG. 1
FIG. 2

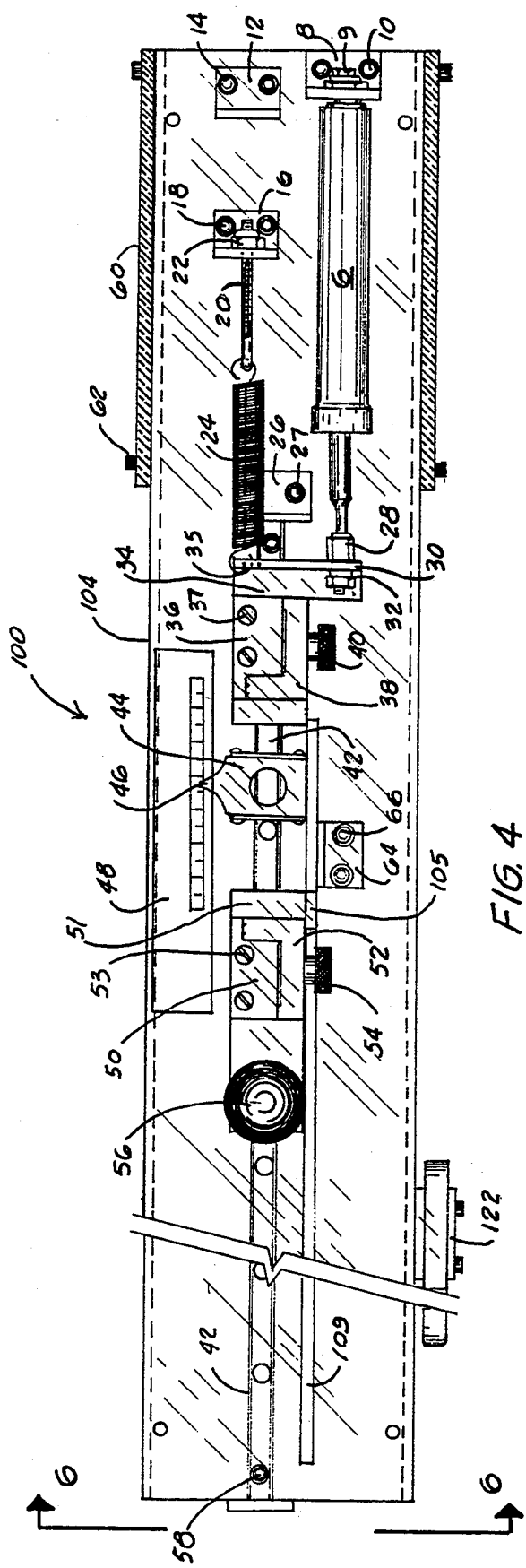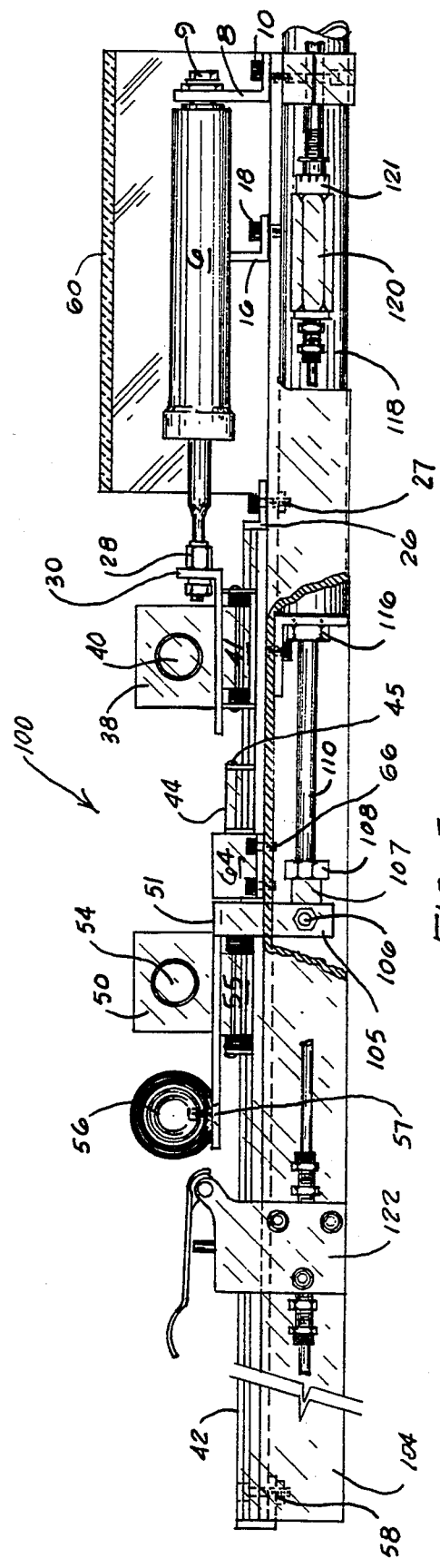

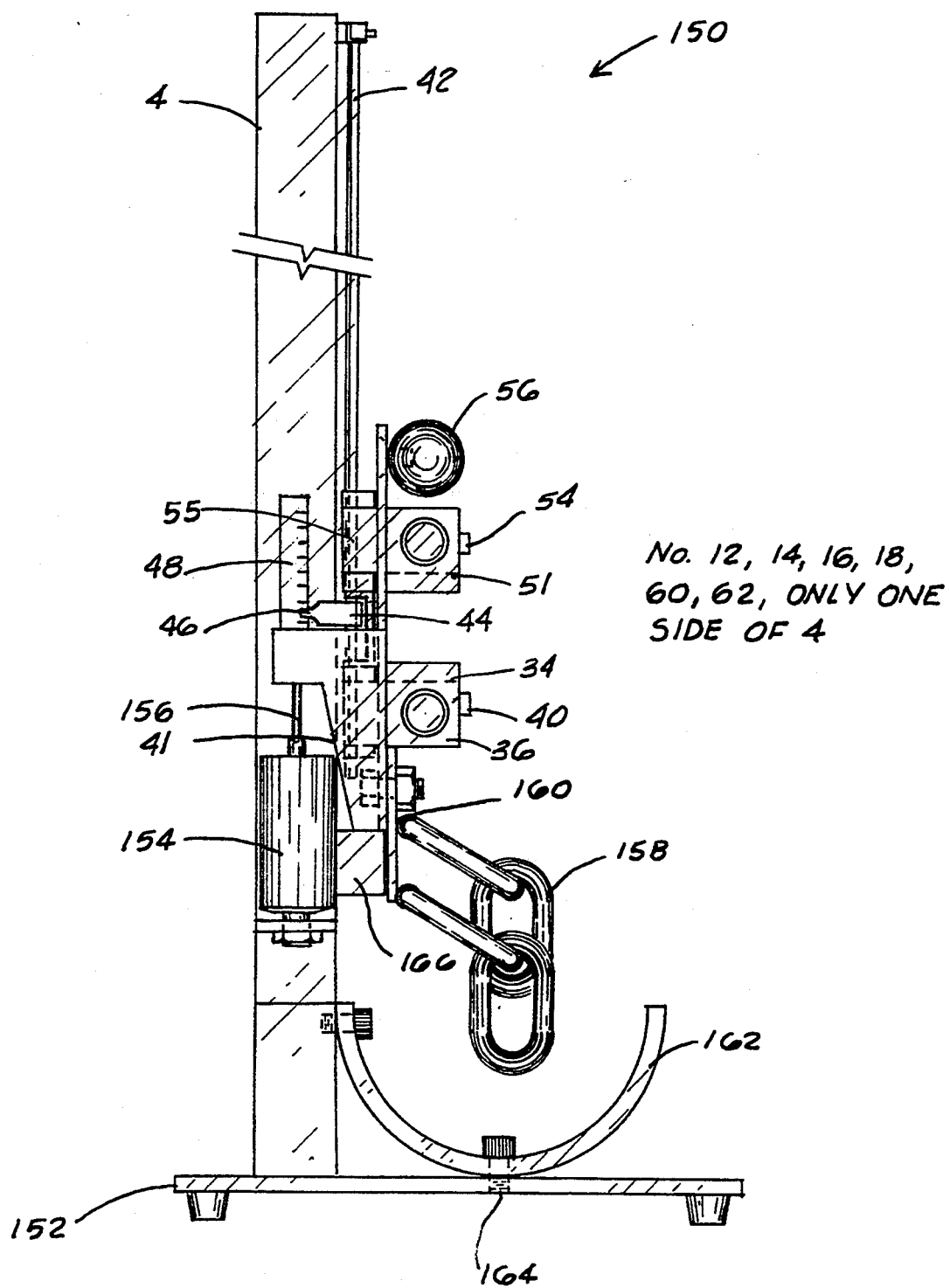

METHOD AND APPARATUS FOR MEASURING THE PEEL STRENGTH OF AN ADHESIVELY BONDED PAPER JOINT

BACKGROUND OF THE INVENTION

1. Field of the Invention

This invention relates to an apparatus and method for measuring the peel strength of a paper joint which is adhesively bonded. Such structures of this type, generally, allow the peel strength of the adhesively bonded joint to be accurately and repeatably measured in an inexpensive manner.

2. Description of the Related Art

It is known, in adhesive bond testing systems, to make use of a device which tests the tensile strength of the adhesive bond. Exemplary of such prior art tensile testing systems are U. S. Pat. Nos. 4,893,513 to Schroeder et al. and 5,201,230 to Sakakibara. While these tensile testers are capable of measuring the tensile strength required to pull apart an adhesive bond, these testers do not adequately measure the strength applied to "peel" apart the paper members which are adhered together by the bond. It is important to know the "peel" strength of the bond in order to more adequately determine the strength of the bond between the adhered paper members. Also, these testers are prohibitively expensive due to the complexity of their construction. Therefore, a more advantageous adhesive bond testing system would be one which inexpensively measures the peel strength instead of the tensile strength.

It is also known, in glue bond testing systems, to make use of a peel strength tester. Exemplary of such peel strength testers are U. S. Pat. Nos. 3,850,033 to Schmitt and 4,080,825 to Liebrenz et al. While these peel strength testers measure the peel strength of a glue bond, these testers employ motors. Consequently, the system is only as reliable as the motor. If the motor fails, then the system cannot be operated. Also, these testers are prohibitively expensive due to the complexity of their construction. Therefore, a still further advantageous glue bond tester would be one which can inexpensively test the peel strength of the glue bond while avoiding the use of a motorized tester.

It is apparent from the above that there exists a need in the art for an adhesive bond tester which is inexpensive through simplicity of parts and uniqueness of structure and which is capable of measuring the peel strength of the adhesive bond, but at the same time avoids the use of a motorized system. It is the purpose of this invention to fulfill this and other needs in the art in a manner more apparent to the skilled artisan once given the following disclosure.

SUMMARY OF THE INVENTION

Generally speaking, this invention fulfills these needs by providing an apparatus for measuring a peel strength of an adhesive joint comprising a paperboard means having first and second sides including an adhesive joint substantially located between the first and second sides, a base means, a force exerting means operatively connected at one end to the base means, a first clamping means operatively connected to the other end of the force exerting means and the first side of the paperboard means, a guiding means operatively connected to the base means and the first clamping means, a second clamping means operatively connected to the second side of the paperboard means and the guiding means, a peel strength indicating means operatively connected to the guiding means and located substantially between the first and second clamping means, and a linear translation means operatively connected to the second clamping means for peeling the first and second sides of the paperboard means away from each other along the adhesive joint to determine the peel strength of the adhesive joint.

In certain preferred embodiments, the force exerting means is a spring or a chain. Also, the guiding means is a linear rail. Also, the peel strength indicating means is a pointer and a graduated scale. Finally, the linear translation means can either be by a manual movement or a pneumatic or hydraulic piston.

In another further preferred embodiment, the apparatus accurately measures the peel strength of an adhesive joint in a simple and repeatable manner.

The preferred adhesive joint peel strength tester, according to this invention, offers the following advantages: lightness in weight; ease of assembly and repair; excellent peel strength measuring characteristics; good stability; good durability; and excellent economy. In fact, in many of the preferred embodiments, these factors of lightness in weight, ease of assembly and repair, excellent peel strength measuring characteristics, and excellent economy are optimized to an extent that is considerably higher than heretofore achieved in prior, known adhesive joint strength testers.

The above and other features of the present invention, which will become more apparent as the description proceeds, are best understood by considering the following detailed description in conjunction with the accompanying drawings, wherein like characters represent like parts throughout the several views and in which:

BRIEF DESCRIPTION OF THE DRAWINGS

FIG. 1 is a top plan view of an apparatus for measuring the peel strength in an adhesive joint, according to the present invention;

FIG. 2 is a side view of the apparatus for measuring the peel strength of an adhesive joint, according to the present invention;

FIG. 4 is a top plan view of another embodiment of an apparatus for measuring the peel strength of an adhesive joint, according to the present invention;

FIG. 5 is a side view of the apparatus for measuring the peel strength of an adhesive joint, according to the present invention;

FIG. 7 is a plan view of another embodiment of an apparatus for measuring the peel strength of an adhesive joint, according to the present invention.

DETAILED DESCRIPTION OF THE INVENTION

Figure 3:
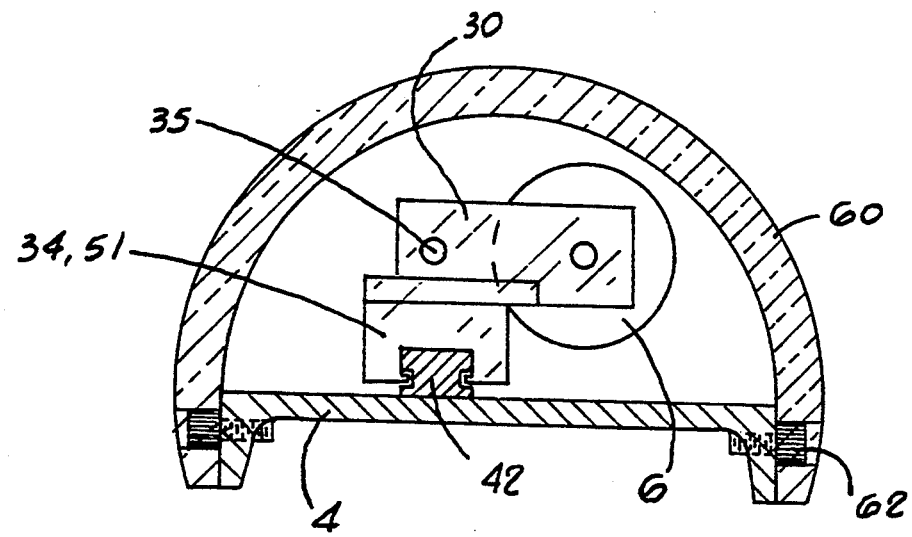
FIG. 3 is an end view, taken along lines 3—3 of FIG. 1, of the apparatus for measuring the peel strength of an adhesive joint, according to the present invention.

With reference first to FIG. 1, there is illustrated apparatus 2 for measuring the peel strength of an adhesive joint between two pieces of paperboard that are adhesively bonded. Apparatus 2 includes, in part, base 4, conventional dashpot 6, conventional spring 24, clamping mechanism 34, linear rail 42, pointer 44, graduated scale 48 and clamping mechanism 51.

In particular, dashpot 6 is rigidly attached to base 4 through conventional bracket 8 by conventional fasteners 9 and 10. The other end of dashpot 6 is attached to bracket 30 by conventional fasteners 28 and 32.

Conventional bracket 12 is rigidly attached to base 4 by conventional fasteners 14. Spring 24 attaches to bracket 12 using conventional eye bolt 20. The other end of spring 24 hooks onto bracket 26. Eye bolt 20 can be used to adjust the force exerted by spring 24. Bracket 12 may also be mounted in position 16 so that a longer spring having a lower spring constant (K) may be used.

Bracket 26 is rigidly attached to base 4 by conventional fasteners 27. Bracket 26 is rigidly attached to clamping mechanism 34 by conventional fasteners 37.

With respect to clamping mechanism 34, clamping mechanism 34 includes, support plate 36, clamping plate 38 and thumbscrew 40. Thumbscrew 40 is located such that clamping plate 38 comes into contact with support plate 36. Clamping mechanism 34 is slidably attached to conventional linear rail 42 by conventional sliding block 41 (FIG. 2).

Located adjacent to clamping mechanism 34 is sliding pointer 44. Pointer 46 is located on sliding pointer 44. Sliding pointer 44 is slidingly attached to rail 42 by conventional sliding block 45 (FIG. 2). A conventional graduated scale 48, which measures the peel strength force in pounds (LBF), is located adjacent to pointer 46.

Conventional stop 64 is rigidly attached to base 4 by conventional fastener 66. Bracket 64 is used to stop the forward motion of sliding pointer 44 along rail 42.

Another clamping mechanism 51 is located adjacent to sliding pointer 44. Clamping mechanism 51 is similar in construction to clamping mechanism 34. In particular, clamping mechanism includes, support plate 50, clamping plate 52, conventional fasteners 53, and thumbscrew 54. As with clamping mechanism 34, fasteners 53 are used to connect support plate 50 to clamping mechanism 51. Thumbscrew 54 is used to hold clamping plate 52 against support plate 50. Handle 56 is used to slide clamping mechanism 51 along rail 42 through the use of conventional sliding block 55 (FIG. 2).

Finally, conventional fastener 58 is used to rigidly attached rail 42 to base 4. Conventional fasteners 62 are used to rigidly attach a conventional shield 60 to base 4. Preferably, shield 60 is constructed of any suitable clear polymeric material, such as, Plexiglas ®.

With respect to FIG. 2, FIG. 2 shows that handle 56 is rigidly attached to clamping mechanism 51 by conventional fasteners 57.

Finally, FIG. 3 shows the alignment of dashpot 6, bracket 30, clamping mechanisms 34 and 51, and rail 42.

During the operation of apparatus 2, a test sample which consist of two pieces of paperboard having an adhesive joint located between the two pieces of paperboard is placed in clamping mechanisms 34 and 51. The two pieces of paperboard are adhesively bonded such that the pieces are located in a parallel relationship with each other and the ends of the paperboard are not adhered so that the ends can be pulled away from each other to determine a peel strength of the adhesive joints between the two pieces of paperboard.

In particular, one end of the paperboard sample is placed between support plate 36 and clamping plate 38 of clamping mechanism 34. Thumbscrew 40 is rotated such that clamping plate 38 is clamped against support plate 36 and that end of the paperboard sample is clamped in clamping mechanism 34. The other end of the paperboard sample is clamped between support plate 50 and clamping plate 52 of clamping mechanism 51 in much the same manner.

Clamping mechanism 34 is restrained by spring 24 and clamping mechanism 51 is manually pulled to separate the sample at the adhesive joint in order to determine the peel strength of the adhesive joint. As discussed earlier, clamping mechanisms 34 and 51 are mounted on conventional sliding blocks 41 and 55, respectively, along rail 42. This enables precise alignment of clamping mechanisms 34 and 51 to be maintained while the test samples are pulled apart, which is important to the accuracy and repeatability of the physical process.

This accuracy is also enhanced by the low friction coefficient of rail 42. The uniformity of the test results is also enhanced by how the test samples are mounted in the clamping mechanisms 34 and 51. The geometry of clamping plates 38 and 52 with respect to support plates 36 and 50, respectively, is such that a sample is inserted at a maximum, fixed distance each time. As discussed earlier, clamping mechanisms 34 and 51 are clamped shut when thumbscrews 40 and 54, respectively, are tightened. A conventional compression spring (not shown) inside each clamping mechanism 34 and 51 opens the clamping mechanism 34 and 51 when thumbscrews 40 and 54, respectively, are loosened.

Motion of the spring-restrained clamping mechanism 34 is dampened by dashpot 6. In this manner, dashpot 6 smoothes out oscillations caused by small variations in the force as the sample peels and slows down the return of clamping mechanism 34 after the sample has been separated.

The elongation of spring 24 attached to clamping mechanism 34 is a measure of the force sustained across the sample as the sample is peeled or separated. Sliding pointer 44 registers a maximum travel of the spring-restrained clamping mechanism 34. The graduated scale 48 converts the position of pointer 46 into units of force, namely, pounds (LBF). Measurement "span" is fixed by the stiffness of spring 24. Measurement "zero" equals the initial tension of spring 24 and can be adjusted by means of the eye screw 24 and fastener 22. All components of the instrument, namely, base 4, clamping mechanisms 34 and 50, mounting brackets 8, 12, 16, 26 and 30, and rail 42 are constructed of aluminum.

With respect to FIGS. 4 and 5, FIGS. 4 and 5 illustrate another embodiment of an apparatus 100 for measuring a peel strength of an adhesive joint between two paperboard sheets which are adhesively bonded. Apparatus 100 is constructed substantially the same as apparatus 2 of FIGS. 1-3. However, apparatus 100 also includes, in part, base 104, extension 105, conventional fastener 106, extension 107, conventional fastener 108, slot 109, actuator rod 110, bracket 112, conventional fastener 114, fastener 116, actuator 118, flow regulator 120, flow rate indicator 121, and conventional air inlet valve 122.

In particular, bracket 105 is an extension of clamping mechanism 51. Bracket 105 is rigidly attached to extension 107 by conventional fastener 106. Extension 107 is rigidly attached to actuator rod 110 by conventional fastener 108. Extension 107 extends through base 104 along conventionally machined slot 109. Actuator 118 is rigidly attached to apparatus 100 by conventional bracket 112 and fastener 116. Bracket 112 is rigidly attached to base 4 by conventional fastener 114.

Conventional air regulation device 120 is rigidly attached to actuator 118 by conventional fasteners (not shown). Air regulation device 120 includes air flow rate indicator 121. Located at the other end of actuator 118 is the conventional air inlet valve 122.

Figure 6:
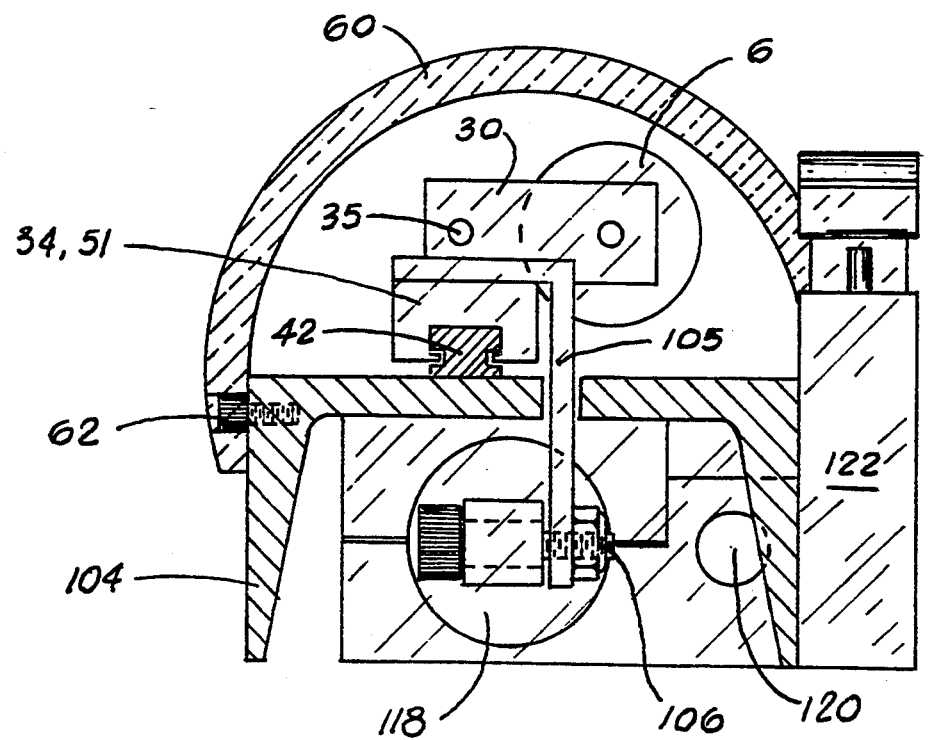
FIG. 6 is an end view, taken along lines 6—6 of FIG. 4, of the apparatus for measuring the peel strength of an adhesive joint, according to the present invention.

With respect to FIG. 6, FIG. 6 shows the alignment of various parts of apparatus 100. In particular, FIG. 6 shows the alignment of dashpot 6, bracket 30, clamping mechanisms 34 and 51, rail 42, base 104, bracket 105, fastener 106, actuator 118, flow regulator 120 and air inlet valve 122. Finally, base 104, bracket 105, extension 107, and bracket 112, preferably, are constructed of aluminum.

The operation of apparatus 100 is substantially similar to the operation of apparatus 2. However, due to the fact that if the operator of apparatus 2 jerks or yanks the clamping mechanism 51 in order to perform the test on apparatus 2, instead of using a steady, reasonably slow (greater than ¼ second duration) pull, an erroneous result may be obtained. An extremely fast pull can yield a false low test value because the spring/mass system of the spring-restrained clamping mechanism 34 (FIG. 1) has no time to deflect to the equilibrium value that represents the actual spring force. Also, a false high value can be obtained because the sliding pointer 44 (FIG. 1) that should register the maximum travel of the spring-restrained clamping mechanism 34 moves so fast that it "coasts" past the point of maximum travel.

In order to eliminate any influence of different test procedures practiced by different operators, the embodiment as set forth in FIGS. 4–6 may be utilized. The clamping mechanism that was originally designed to be pulled by the hand, namely, clamping mechanism 51, can also be moved using a hydraulic or pneumatic cylinder 118. In this manner, the speed of the test pull can be regulated and fixed to a desired constant value. In particular, pneumatic or hydraulic cylinder 118 is fed from air supply valve 122. Air supply flow rate can be regulated by flow regulator 120 and flow rate indicator 121. The air supply pressure value is regulated so that the force generated by the cylinder 118 is more than great enough to separate any test sample. The flow rate is set to yield the desired cylinder stroke speed. A hand-operated valve 122 on the air supply line can be opened to move the cylinder and perform the pull test.

Finally, FIG. 7 shows still another embodiment of an apparatus 150 for measuring the peel strength of an adhesive joint between two paperboard sheets which are adhesively bonded. In particular, apparatus 150 is constructed substantially the same as apparatus 2 and 100. However, apparatus 150 also includes base 152, snubber 154, extension 156, conventional chain 158, conventional chain clamping mechanism 160, chain tray 162 and conventional fastener 164.

The operation of apparatus 150 is essentially the same as operation of apparatus 2 and 100. In particular, the test sample is firmly held in clamping apparatus 34 and 51. Clamping apparatus 34 is rigidly attached to chain 158 by mechanism 160. The clamping mechanism 51 is pulled, either manually or mechanically in order to separate the sample and perform the test. Clamping mechanisms 34 and 51 are mounted on conventional sliding blocks as discussed earlier with respect to FIGS. 1–6. This enables precise alignment of clamping mechanisms 34 and 51 to be maintained while the test sample is pulled apart which is important to the accuracy and repeatability of the physical test.

Test accuracy is also enhanced by the low friction coefficient of rail 42 (the actual test value to be diminished by the frictional force that restrains free translation of the chain-weighted clamping mechanism 34).

Uniformity of the test results is also influenced by how the test samples are mounted in the clamping mechanisms 34 and 51, namely, the geometry of the clamping mechanisms is such that the sample is inserted at a maximum, fixed distance each time. Clamping mechanisms 34 and 51 are clamped shut when the thumbscrews 40 and 54, respectively, are tightened. A compression spring (not shown) inside each clamping mechanism 34 and 51 opens each clamping mechanisms 34 and 51 when thumbscrews 40 and 54, respectively, are loosened.

A conventional one-way snubber 154 slows down the return of the chain-weighted clamping mechanism 34 after the sample has been separated. Stop 166 keeps clamping mechanism 34 from exceeding a lowest point limit. The test load sustained by the sample is equal to the combined weight of the lower clamping mechanism 34 plus the length of the suspended chain 158.

A sliding pointer 44 registers the maximum upward travel of the lower clamping mechanism 34 and a graduated scale 48 converts the position of pointer 46 into units of force, namely, pounds (LBF).

Measurement "span" is fixed by the size (or weight per unit length) of chain 158. Measurement "zero" equals the combined weight of the lower clamping mechanism 34 plus the length of chain 158 suspended from the clamping mechanism 34 when clamping mechanism 34 is in its lower-most position. An advantage of apparatus 150 is that its calibration (for a given chain size) cannot change. Base 152 and tray 162, preferably, are constructed of aluminum.

A further simplification of apparatus 150 may eliminates the pointer 44, column 4, and clamping mechanism 51. In this manner only the essential items would be lower clamping mechanism 34 which is attached to chain 158 with the other end of the sample being gripped by the operator's hand. In this manner, the test sample is lifted until the weight of the chain 158 that is lifted from tray 162 defines the glue line peel strength. Chain 158 could be color coded or otherwise designated so that, with observation during the lift, the peak force could be determined.

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. An apparatus for measuring a peel strength of an adhesive joint comprised of:
   a paperboard means having first and second sides including an adhesive joint substantially located between said first and second sides;
   a base means;
   a force exerting means operatively connected at one end to said base means wherein said force exerting means is further comprised of a weight means;
   a first clamping means operatively connected to another end of said force exerting means and said first side of said paperboard means;

a guiding means operatively connected to said base means and said first clamping means;

a second clamping means operatively connected to said second side of said paperboard means and said guiding means;

a peel strength indicating means operatively connected to said guiding means and located substantially between said first and second clamping means; and a linear translation means operatively connected to said second clamping means for peeling said first and second sides of said paperboard means away from each other along said adhesive joint to determine said peel strength of said adhesive joint.

2. The apparatus, as in claim 1, wherein said force exerting means is further comprised of:

a spring means.

3. The apparatus as in claim 1, wherein said weight means is further comprised of:

a chain.

4. The apparatus, as in claim 1, wherein said apparatus is further comprised of:

a force dampening means operatively connected to said base means and said first clamping means.

5. The apparatus, as in claim 4, wherein said force dampening means is further comprised of:

a dashpot.

6. The apparatus, as in claim 4, wherein said force dampening means is further comprised of:

a snubber.

7. The apparatus, as in claim 1, wherein said paperboard means is further comprised of:

first and second paperboard sheets located in a substantially parallel position with respect to each other;

an adhesive joint located substantially between said paperboard sheets; and areas located along said first and second paperboard sheets which are separated away from each other and located adjacent to said adhesive joint.

8. The apparatus, as in claim 1, wherein said first clamping means is further comprised of:

a sliding means;

a support plate means operatively connected to said sliding means;

a clamping plate means operatively connected to said sliding means; and a fastener means operatively connected to said support plate means and said clamping plate means.

9. The apparatus, as in claim 1, wherein said second clamping means is further comprised of:

a sliding means;

a support plate means operatively connected to said sliding means;

a clamping plate means operatively connected to said sliding means; and a fastener means operatively connected to said support plate means and said clamping plate means.

10. The apparatus, as in claim 2, wherein said spring means is further comprised of:

a spring force adjustment means.

11. The apparatus, as in claim 10, wherein said adjustment means is further comprised of:

an eye bolt.

12. The apparatus, as in claim 1, wherein said guiding means is further comprised of:

a rail means.

13. The apparatus, as in claim 1, wherein said peel strength indication means is further comprised of:

a sliding pointer; and a graduated scale located adjacent to said sliding pointer.

14. The apparatus, as in claim 1, wherein said linear translation means is further comprised of:

a manual translation means.

15. The apparatus, as in claim 1, wherein said linear translation means is further comprised of:

a pneumatic translation means.

16. The apparatus, as in claim 1, wherein said linear translation means is further comprised of:

a hydraulic translation means.

17. A method of measuring a peel strength of an adhesive joint located between two paperboard sheets, including a paperboard sheet means having an adhesive joint between said sample sheet means and first and second ends located adjacent to said adhesive joint and substantially parallel to each other, first and second clamping means, a force exerting means, a force dampening means, a peel strength indicating means, and a linear translation means, wherein said method is comprised of the steps of:

clamping said first end of said paperboard sheet means in said first clamping means;

clamping said second end of said paperboard sheet means in said second clamping means;

translating said second clamping means by said linear translation means;

exerting a force on said first clamping means by said force exerting means;

regulating a force of said force exerting means by said force dampening means;

peeling said first and second ends of said paperboard sheet means away from each other in order to breakup said adhesive joint;

dampening a return force of said first clamping means; and measuring a peel strength of said adhesive joint by said peel strength indicating means.

18. The method, as in claim 17, wherein said step of translating said clamping means is further comprised of the step of:

manually translating said second clamping means.

19. The method, as in claim 17, wherein said step of translating said clamping means is further comprised of the step of:

pneumatically translating said second clamping means.

20. The method, as in claim 17, wherein said step of translating said clamping means is further comprised of the step of:

hydraulically translating said second clamping means.

* * * * *